(12) United States Patent
Gleason et al.

(10) Patent No.: US 7,618,590 B2
(45) Date of Patent: Nov. 17, 2009

(54) FLUID DISPENSING SYSTEM

(75) Inventors: K. Reed Gleason, Portland, OR (US); Peter Navratil, Portland, OR (US); John Martin, Portland, OR (US); John Dunklee, Tigard, OR (US); Cali Sartor, Aloha, OR (US); Thane Allison, Hillsboro, OR (US)

(73) Assignee: Cascade Microtech, Inc., Beaverton, OR (US)

( * ) Notice: Subject to any disclaimer, the term of this patent is extended or adjusted under 35 U.S.C. 154(b) by 305 days.

(21) Appl. No.: 11/474,723

(22) Filed: Jun. 26, 2006

(65) Prior Publication Data

US 2007/0003447 A1 Jan. 4, 2007

Related U.S. Application Data

(60) Provisional application No. 60/695,610, filed on Jun. 29, 2005.

(51) Int. Cl.
*B01L 3/02* (2006.01)
(52) U.S. Cl. .................. 422/100; 422/103; 422/104
(58) Field of Classification Search ........... 422/99–104; 436/179, 180; 73/863.31, 863.32
See application file for complete search history.

(56) References Cited

U.S. PATENT DOCUMENTS

| | | | |
|---|---|---|---|
| 3,832,579 A | 8/1974 | Arndt | |
| 5,656,034 A | 8/1997 | Kochersperger et al. | |
| 5,927,547 A | 7/1999 | Papen et al. | |
| 6,024,925 A * | 2/2000 | Little et al. | 422/100 |
| 6,207,031 B1 * | 3/2001 | Adourian et al. | 204/451 |
| 6,209,928 B1 | 4/2001 | Benett et al. | |
| 6,273,478 B1 | 8/2001 | Benett et al. | |
| 6,322,752 B1 * | 11/2001 | Siddiqui et al. | 422/100 |
| 6,488,892 B1 * | 12/2002 | Burton et al. | 422/82.05 |
| 6,581,899 B2 | 6/2003 | Williams | |
| 6,620,625 B2 * | 9/2003 | Wolk et al. | 436/180 |
| 6,627,446 B1 * | 9/2003 | Roach et al. | 436/43 |
| 6,692,972 B1 * | 2/2004 | Yershov et al. | 436/180 |
| 6,709,559 B2 | 3/2004 | Sundberg et al. | |
| 6,813,844 B1 | 11/2004 | Steinich | |
| 6,832,787 B1 | 12/2004 | Renzi | |
| 7,213,473 B2 * | 5/2007 | Mosier et al. | 73/861.52 |
| 2001/0001474 A1 * | 5/2001 | Moon et al. | 239/3 |
| 2005/0106066 A1 | 5/2005 | Saltsman et al. | |

OTHER PUBLICATIONS

Holl, Mark et al., Microfluidic Materials: Polymeric Laminate Technology, Aug. 9, 2004, http://faculty.washington.edu/yagerp/microfluidicstutorial/polymericlaminates/polymericlaminates.htm, University of Washington, Seattle.

Yager, Paul; A New Microfluidic Paradigm for Biological and Biochemical Research, Sep. 2, 2003, http://faculty.washington.edu/yagerp/microfluidicstutorial/newparadigm/newparadigm.htm, University of Washington, Seattle.

(Continued)

*Primary Examiner*—Jill Warden
*Assistant Examiner*—Dwayne K Handy
(74) *Attorney, Agent, or Firm*—Chernoff, Vilhauer, McClung & Stenzel (57) ABSTRACT

A fluid dispensing apparatus and system for facilitating dispensing small volume, fluid samples to microfluidic devices.

2 Claims, 9 Drawing Sheets

OTHER PUBLICATIONS

Schilling, Eric, Basic Microfluidic Concepts, Aug. 9, 2004, http://faculty.washington.edu/yagerp/microfluidicstutorial/basicconcepts/basicconcepts.htm, University of Washington, Seattle.

Brody, James et al., The H-Filter, Sep. 2, 2003, http://faculty.washington.edu/yagerp/microfluidicstutorial/hfilter/hfilterhome.htm, University of Washington, Seattle.

Schilling, Eric et al., The T-Sensor, Sep. 2, 2003, http://faculty.washington.edu/yagerp/microfluidicstutorial/tsensor/tsensor.htm, University of Washington, Seattle.

Hatch, Anson et al., Diffusion Immunoassay (DIA), Aug. 9, 2004, http://faculty.washington.edu/yagerp/microfluidicstutorial/dia/diffusionimmunoassayhome.htm, University of Washington, Seattle.

Cabrera, Catherine et al., Transverse Electrophoresis and Isoelectric Focusing (IEF), Sep. 2, 2003, http://faculty.washington.edu/yagerp/microfluidicstutorial/transverseief/transverseief.htm, University of Washington, Seattle.

Oulellette, Jennifer, A New Wave of Microfluidic Devices, The Industrial Physicist, Aug./Sep. 2003, pp. 14-17, The American Institute of Physics, USA.

Meng, Ellis, Silicon Couplers for Microfluidic Applications, Jul. 31, 2001, pp. 270-275, California Institute of Technology, Pasadena.

Pattekar, Ashish et al., Novel Microfluidic Interconnections for High Temperature and Pressure Applications, Journal of Micromechanics and Microengineering, Feb. 13, 2002, Institute of Physics Publishing, UK.

\* cited by examiner

FLUID DISPENSING SYSTEM

CROSS-REFERENCE TO RELATED APPLICATIONS

This application claims the benefit of U.S. Provisional Application No. 60/695,610, filed Jun. 29, 2005.

BACKGROUND OF THE INVENTION

The present invention relates to an apparatus and system for dispensing fluids and, more particularly, an apparatus and system for dispensing small volume fluid samples to microfluidic devices.

A recent development in analytical testing has been the miniaturization of testing equipment used to detect and analyze the constituents of samples of chemical and biological fluids. Using tools and techniques developed for producing electronic devices, intricate microfluidic systems can be inexpensively mass produced. Improved performance, reduced time, reduced reagent consumption, enhanced availability and ability to automate have provided impetus for the development of "microfluidic" or "micro-total analysis" devices and systems, also commonly referred to as a "lab-on-a-chip."

Microfluidic devices are typically constructed by laminating multiple layers of glass, silicon, metal, polymer and other organic and inorganic materials. One of more of the layers includes microscale structures and voids such that when the layers are assembled microfluidic channels are formed for the flow and storage of fluid in the device. A microscale or microfluidic channel is generally a fluid passage which has at least one internal cross-sectional dimension that is less than 500 micrometers ($\mu$m) and, commonly, has at least one internal cross-sectional dimension less than 100 $\mu$m. Electrodes may be connected to one or more layers of the device to enable connecting an external power source, instrument or control to a transducer or other circuit formed on a layer of the device. Very small samples of liquids and gases, typically, a few nanoliters, introduced to or stored in the microfluidic device may be mixed, reacted or separated from a reagent for the purposes of performing a chemical or physical analysis of the fluid sample.

The movement and control of fluid flow in the channels of the microfluidic device may be accomplished by either forcing pressurized fluid into the device with an external pump or by pressurizing the fluid with a pump(s) built into the microfluidic device. The pressure differential to move fluid within the microfluidic device may be provided by a number of fluid drivers, such as a piezoelectric pump, micro-syringe pump or electroosmotic pump, that may be mounted internal or external to the device. However, a microfluidic device may also utilize a chemically induced pressure differential or inherent fluid force, such as gravity, hydrostatic pressure, capillary force, and absorption by a porous material, to produce fluid flow within the device. Microfluidic devices also commonly include active and passive valves to control the flow of fluid. Passive valves such as check valves are activated by the pressure and flow of the fluid. Active valves may be actuated pneumatically, electromechanically, mechanically or manually, to control fluid flow in the microfluidic channels of the device.

Miniscule samples of fluids, such as whole blood, bacterial cell suspensions, protein and antibody solutions, are introduced to the microfluidic device through one or more sample inlets and are mixed, separated and reacted with other substances introduced through other sample inlets or stored in the microfluidic device to determine a characteristic of the sample. Fluid is commonly introduced to the sample inlets of microfluidic devices through a micropipette. However, the small size of the microfluidic device makes manual pipetting of samples difficult and unreliable. On the other hand, automated sample dispensers are expensive and relatively inflexible because the dispensing mechanism must be programmed to position the fluid dispenser over the sample inlet of each type of microfluidic device or titer plate. In addition, pipetting is not suitable if the sample is to be injected under pressure because the sample inlet is not sealed. If the sample is to be introduced under pressure, the capillary tube used to deliver the sample is often cemented in the sample inlet well or into a ferrule which can be pressed into the sample inlet well of the device. What is desired, therefore, is a fluid dispensing system that can be accurately, freely and flexibly positioned to accurately dispense small samples of fluids to the sample inlet wells of a variety microfluidic devices.

DETAILED DESCRIPTION OF PREFERRED EMBODIMENTS

Figure 1:
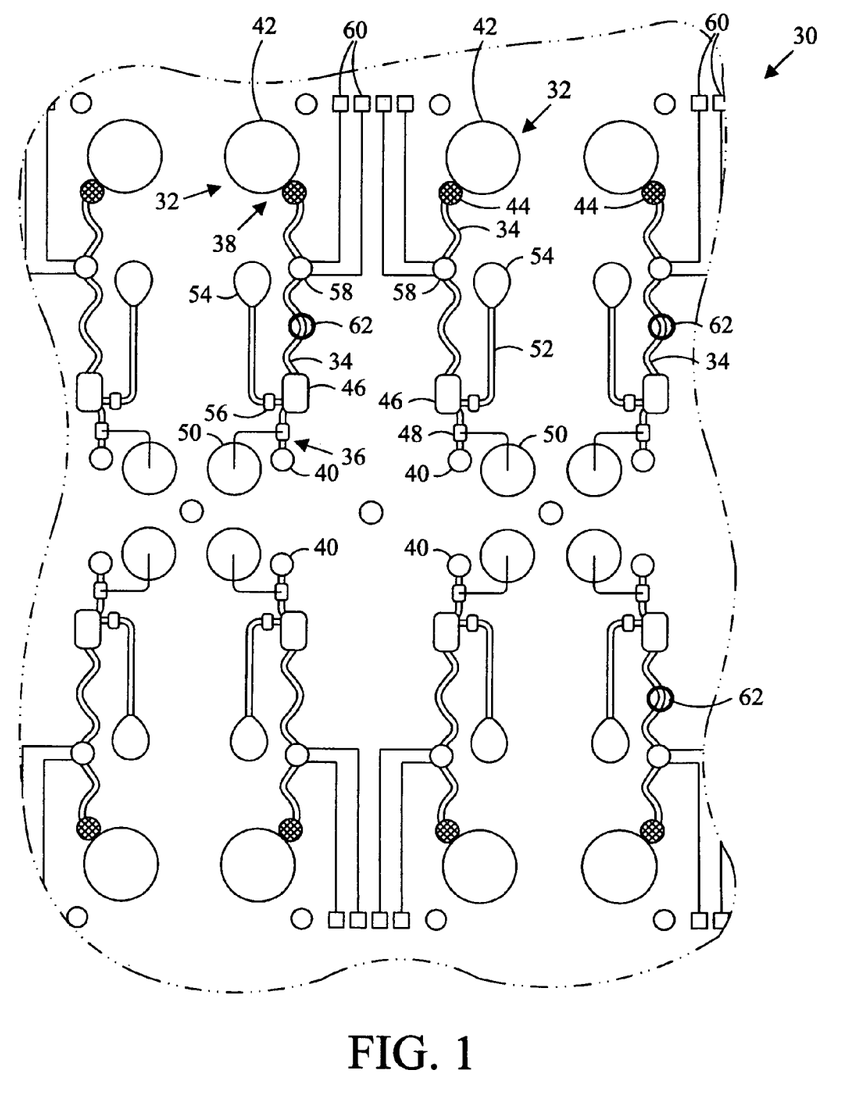
FIG. 1 is a top view of a portion of a exemplary microfluidic structure comprising a plurality of schematic microfluidic devices.

Referring in detail to the drawings where similar parts are identified by like reference numerals, and, more particularly to FIG. 1, a microfluidic structure 30 comprises one or more microfluidic devices 32. Microfluidic devices may be used to perform a wide variety of tasks and, therefore, comprise an extremely wide variety of arrangements of elements for transporting, controlling and analyzing small quantities of fluid. FIG. 1 is intended to illustrate some of the elements and features of a microfluidic device but is not intended to illustrate a particular device or suggest a particular or actual arrangement of elements. The exemplary microfluidic device 32 comprises a microfluidic channel 34 having a first end 36 and a second end 38. A sample inlet well 40 for receiving a liquid sample is fluidly connected to the first end 36 of the microfluidic channel 32. While fluid flow in a microfluidic device may be the result of a pressure differential produced by a fluid driver external to the device, the exemplary microfluidic device also includes a pump 42, for example a manually, piezoelectrically or mechanically operable bellows pump. The pump 42 is fluidly connected to the second end 38 of the microfluidic channel 34. A liquid barrier 44, for example a gas permeable and liquid impermeable membrane, is interposed between the pump 42 and the second end of the microfluidic channel.

The microfluidic channel 32 fluidly connects the sample inlet well 40 to a microfluidic apparatus 46, for example a T-sensor or an H-filter, and to the pump. A T-sensor comprises microfluidic channels that are arranged to intersect in a tee. Fluids flowing into the arms of the intersection mix in a predicable manner in the outflow of the intersection, the leg of the tee. If, for example, one input stream contains an analyte of interest and the other input comprises a reactor molecule, such as a fluorescent indicator, the chemical binding of the substances produces a measurable reaction, such as fluorescence, which can be used to calculate a parameter of interest, such as a concentration or a diffusion coefficient, for the analyte. On the other hand, an H-filter comprises a pair of inlets and a pair of outlets connected to the first and second ends of a microfluidic channel. A sample fluid containing small molecules and interfering particles is introduced at one inlet and a reagent for the small molecules is introduced at the other inlet. Mixing is controlled in the microfluidic channel connecting the inlets and outlets. The small molecules interact with the reagent and will be separated from the sample fluid while the interfering particles remain in the fluid and flow out of an outlet.

The exemplary microfluidic device 32 also comprises an active valve, for example an on/off valve 48, interposed between the sample inlet well 40 and the first end of the microfluidic channel. An actuator 50 is provided for operating the active, on/off valve. The on/off valve 48 may comprise a flexible diaphragm portion of a wall of the microfluidic channel-that can be deformed by the actuator to block the channel. The actuator 50 may comprise, for example a second pump to exert fluid pressure on the reverse side of the flexible diaphragm or another suitable manual or mechanical apparatus to deform the diaphragm and either block or enable flow in the microfluidic channel. The exemplary microfluidic device 32 also comprises a second microfluidic channel 52 having a first end and a second end. As illustrated, the first end of the second microfluidic channel 52 is fluidly connected to the first microfluidic channel 32 at a location adjacent to the on/off valve 48 and the second end of the second microfluidic channel is fluidly connected to a reservoir 54 that may store a second chemical, such as a reagent, used in the process performed by the microfluidic device. On the other hand, the reagent could be introduced to the microfluidic device through a second sample inlet. A passive valve 56, for example, a valve that opens when the pressure in one branch of the fluid path exceeds the pressure in a second branch of the fluid path, is interposed between the first end of the second microfluidic channel 52 and the first microfluidic channel 34.

During operation, a fluid sample is introduced to a sample inlet well 40. The pump 42 is actuated to produce a negative pressure in the first microfluidic channel 34 and the fluid sample is drawn from the sample inlet well 40 through the on/off valve 48 and into, and through, microfluidic apparatus. Since the fluid pressure in the first microfluidic channel 34 is less than the fluid pressure in the second microfluidic channel 52, the passive valve 56 opens permitting the fluid stored in the reservoir to mix with the sample in the microfluidic apparatus. A detector 58, for example a photo-sensor, may be used to detect the mixing, separation or reaction of the sample and the second chemical permitting useful information about the sample to be obtained. Electrical terminals 60, conductively connected to the detector, a pump or other electromechanical actuator, and providing selective connection to an appropriate instrument, power source or controller, may be formed on the surface or in a well of the microfluidic structure. The microfluidic device may include a light port 62, for example a lens, for observing a light output with a probe mounted photodetector or a light transmissive, fiber optic probe.

Fluid samples are typically input to microfluidic devices by introducing a small volume of the fluid into one or more sample inlet wells 40 in the body of the device. The sample may be manually inserted into the sample inlet well with a titration tube or syringe. However, manual introduction of samples is difficult and unreliable because the sample inlet well is small and difficult to locate and it is difficult to prevent disturbing the microfluidic device if the sample dispensing means comes into contact with the device. In addition, if the sample is to be introduced to the sample well under pressure the well must be sealed. Sample inlet wells of microfluidic devices are typically sealed by permanently attaching, by cementing or otherwise, a fluid delivery tube in the well or by restraining the device and pressing a ferrule, that is attached to the fluid delivery tube, into the well. On the other hand, sample dispensers that automatically position the sample delivery device and inject the sample into the sample inlet well are expensive and typically must be programmed to position the sample dispensing means for each type of microfluidic device or titer plate that is used. The inventors concluded that a sample dispensing system that enabled free movement and accurate positioning of the sample dispensing outlet would be more flexible than an automated system and more accurate than a manual sampling system.

Figure 2:
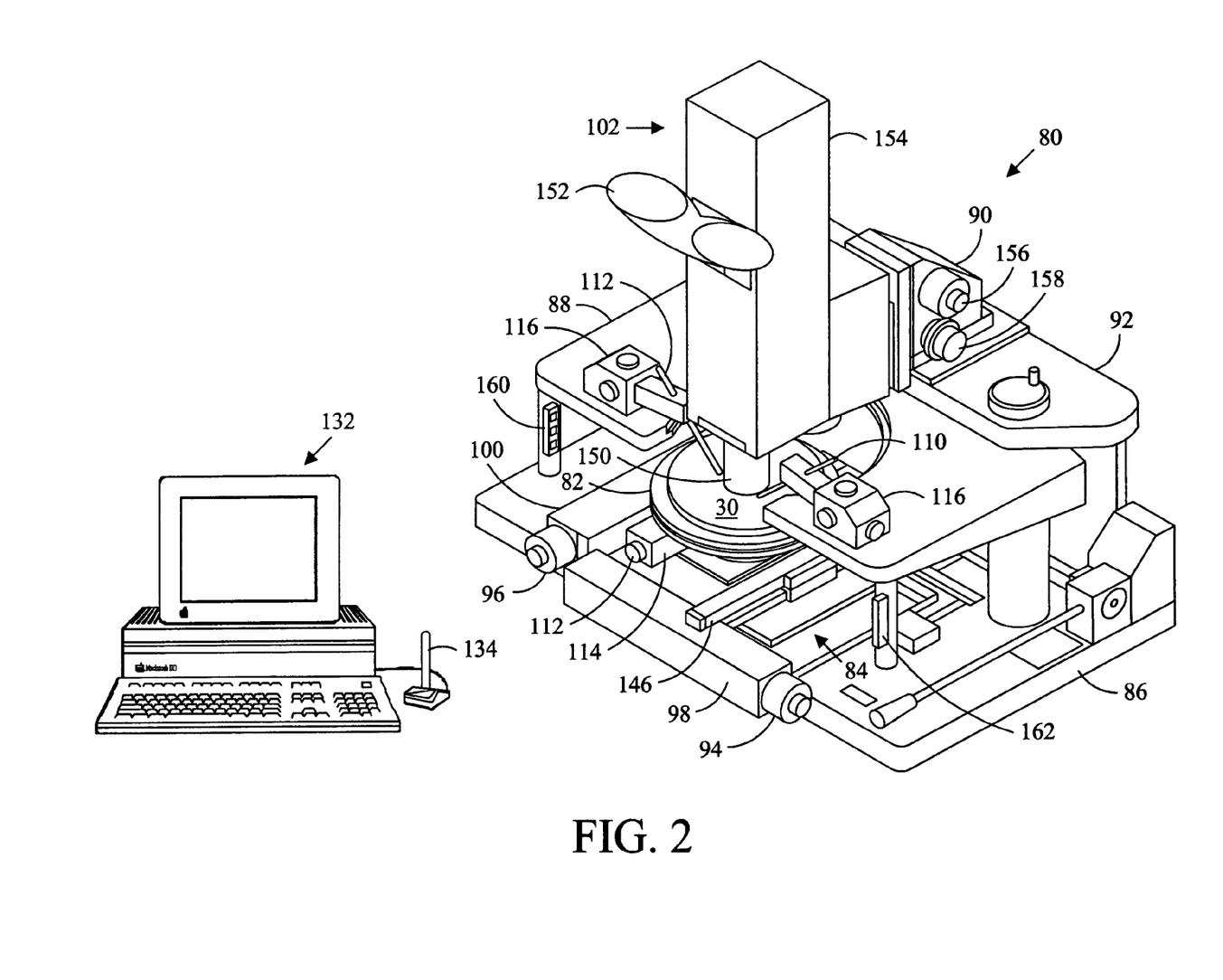
FIG. 2 is a perspective illustration of a fluid dispensing station for use in conjunction with microfluidic devices.
Figure 3:
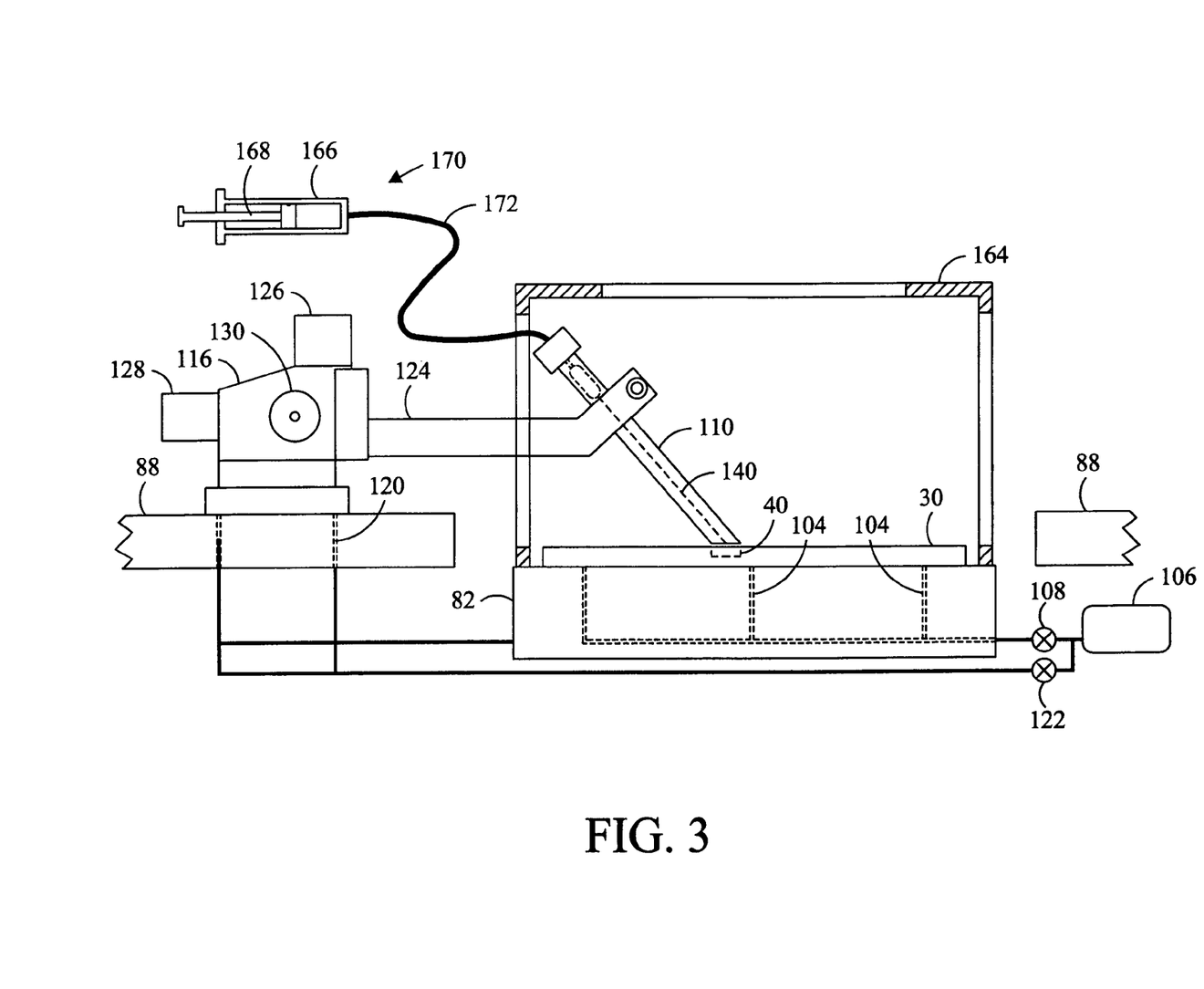
FIG. 3 is a schematic illustration of a first embodiment of a fluid dispensing probe and a chuck of a fluid dispensing station.

Referring to FIGS. 2 and 3, the fluid sample is introduced to the sample inlet well 40 of a microfluidic device 32 in a fluid dispensing station 80. A microfluidic structure 30 comprising one or more microfluidic devices is mounted on a chuck 82 which is supported on a movable stage 84 mounted on a station base 86. The microfluidic structure is restrainable on the upper surface of the chuck 82. The chuck may include a clamp for restraining the microfluidic structure or the upper surface of the chuck may include a plurality of apertures 104 that are selectively connectible to a source of vacuum 106 through a valve 108. When vacuum is connected to the apertures, air pressure, acting on a microfluidic structure resting on the upper surface of the chuck, secures the structure to the chuck's surface.

Fluid dispensing 110 probes and other probes 112, typically, for detecting and transmitting light or electricity are supported over the chuck by a platen 88. The fluid dispensing station 80 is provided with controls for positioning the chuck along horizontal (x and y) axes and the platen 88 may be adjusted in the vertical (z) direction for positioning the probes with respect to the sample inlet wells 40 and other probing points of the microfluidic structure 30. To facilitate relative positioning of the microfluidic structure 30 and the probes, the stage 84 provides for translatory and rotational (theta) movement of the chuck 82. Horizontal translation is accomplished with an x-motor 94 and a y-motor 96 that drive linear actuators 98 and 100 to move the stage 84. A similar mechanism (not shown) provides vertical translation of the chuck 82. Rotation about the vertical axis or fine theta adjustment is provided by a theta motor 112 and an attached linear actuator 114. The theta adjustment is provided to facilitate parallel alignment of the ends of probes with the sample inlet wells and other probing points on the microfluidic device(s).

For additional ease of use, the microfluidic structure 30 may be supported on a indexing rotatable chuck as disclosed by Harris et al., U.S. Pat. No. 6,483,336, incorporated herein by reference. The indexing rotatable chuck permits rapid rotation of a device supported on the chuck to aid in quickly bringing probes into alignment with the sample inlet wells and other probing points that may be laid out in a rectilinear arrangement on a microfluidic structure.

The fluid dispensing 110 probe and other probes are supported on the platen 88 by one or more probe holders 116. The probe holder 116 is typically secured to the platen by a magnetic, vacuum or mechanical fastening mechanism. For example, the platen 88 may include a plurality of apertures 120 selectively connectible to the source of vacuum 106 through a control valve 122. The body of a probe 110 is typically clamped or otherwise secured to an arm 124 that extends from the body of the probe holder 116. Adjustment of the -x, -y, and -z position of the arm 124 relative to the body of the probe holder 116 is typically provided. In addition to manual adjustment, motors 126, 128, 130 may be provided for powered adjustment of the position of the probe under the control of a controller, such as a personal computer 132

By adjusting the position of the probe relative to the probe holder and the relative position of platen and the chuck, a fluid delivery tube 140 of a fluid dispensing probe 110 and the tips of other probes can be aligned with the respective sample inlet wells 40, electrodes 60, light ports 62 or other probing points on a microfluidic device that is secured to the chuck. A data processing system, such as the personal computer 132, may be connected to the various positioning motors of the probe station to provide remote and automated control of the various motions of the probe station elements. For example, a joystick control 134, actuated by the station's operator, and connected to the various positioning motors through appropriate software, may be used to position the chuck and the individual probes. Encoders, such as the linear encoder 146, provide feedback to the data processing system during operation of the stage and probe positioning motors.

To facilitate locating and positioning the probes, the fluid dispensing station 80 includes a optical microscope 102 mounted on a microscope mounting or focus block 90 attached to an optics bridge 92. The microscope 102 includes a back plate that supports the optical elements comprising the optical path of the microscope. With the exception of the objective 150 and the eyepieces 152, optical elements forming the optical path from the lens of the objective to the eyepieces of a binocular optical viewing assembly, are enclosed within a box-like housing 154. The housing 154 may also enclose one or more cameras (not illustrated) for recording and displaying the image viewable through the microscope's optical path.

For focusing, the back plate is attached to a movable microscope mounting plate of the focus block 90 to enable vertical movement of the microscope 102 with respect to the top surface of the chuck 82. Typically, a rack is attached to the microscope mounting plate and a pinion gear, internal to the focus block, engages the rack. The pinion gear is rotatable by a knob 156 to provide manual focusing adjustment. The focus block may also include an electric motor, such as the stepper motor 158, operatively connected to the pinion gear and the microscope mounting surface to provide remotely controlled focusing.

Microfluidic devices may utilize high voltages for certain processes, such as electrophoresis or electroosmosis. The exemplary fluid dispensing station 80 also includes a light curtain comprising one or more light sources 160 and corresponding photo-detectors 162 arranged to detect intrusion into the area of the chuck 82 and, if intrusion is detected, signal a controller to neutralize high voltages or suspend another activity that might pose a threat of injury or damage.

The fluid dispensing station 80 may also include an environmental housing 164 to protect the microfluidic structures mounted on the chuck and the various probes from dust and other environmental hazards.

Figure 4:
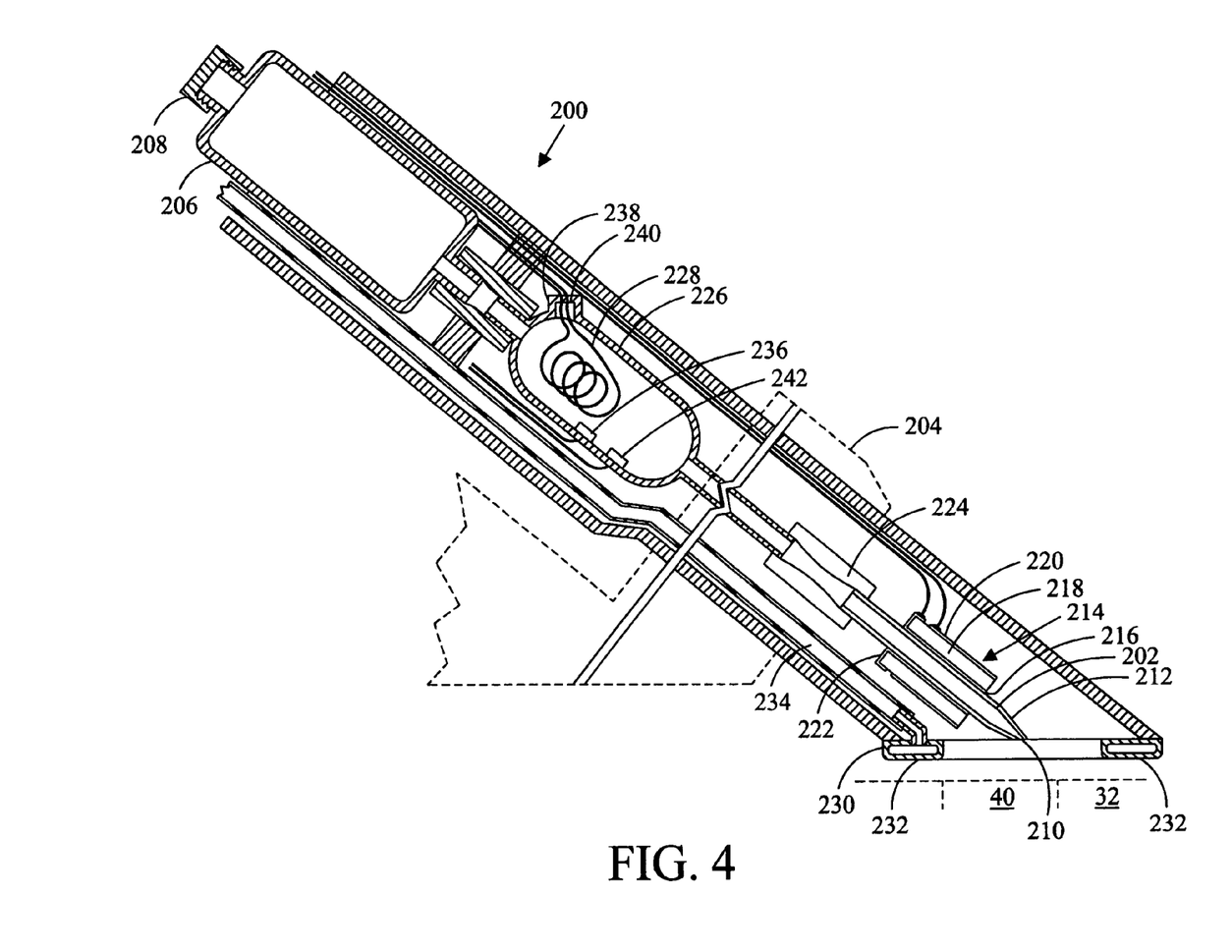
FIG. 4 is a sectional view of a second embodiment of a fluid dispensing probe.

Referring also to FIG. 4, an exemplary fluid dispensing probe 110, 200 comprises one or more fluid delivery tubes 140, 202 secured in a probe holder 124, 204 and positionable in a fluid dispensing station. The fluid delivery tube provides a conduit for delivering a sample of a fluid from a reservoir to a sample inlet well 40 of a microfluidic device 32. The reservoir may be incorporated into the body of the fluid dispensing probe and include a port for selective filling with a syringe or similar device or a probe may be removed from the probe holder and replaced with another probe that includes a pre-filled reservoir. On the other hand, the probe 200 includes a detachable sealable connection 208 permitting removal of the reservoir 206 from the body of the probe for filling at the port 210 and enabling a pre-filled reservoir to be installed in the probe. Or, the reservoir may be separate from the body of the fluid dispensing probe, such as the barrel 168 of a syringe 170, and fluidly connected by a conduit 172 to the fluid delivery tube 140 in the probe.

In addition to the fluid delivery tube and the reservoir, the body of the fluid dispensing probe may include or be connected to a pump or other fluid transfer device. A variety of devices and methods are available for impelling the flow of fluid from the fluid delivery tube to the sample inlet well of a microfluidics device. As illustrated in FIG. 3, a manually operated syringe 170 may be connected to the fluid delivery tube 140 of the fluid dispensing probe 110. The syringe comprises a barrel 166 and a plunger 168 that is fluidly sealed to the barrel but slidable in the barrel. When the operator of the fluid dispensing station exerts a manual force to displace the plunger, the volume for fluid in the barrel is reduced and fluid is forced out of the barrel and through the fluid delivery tube to the sample inlet well.

Figure 5:
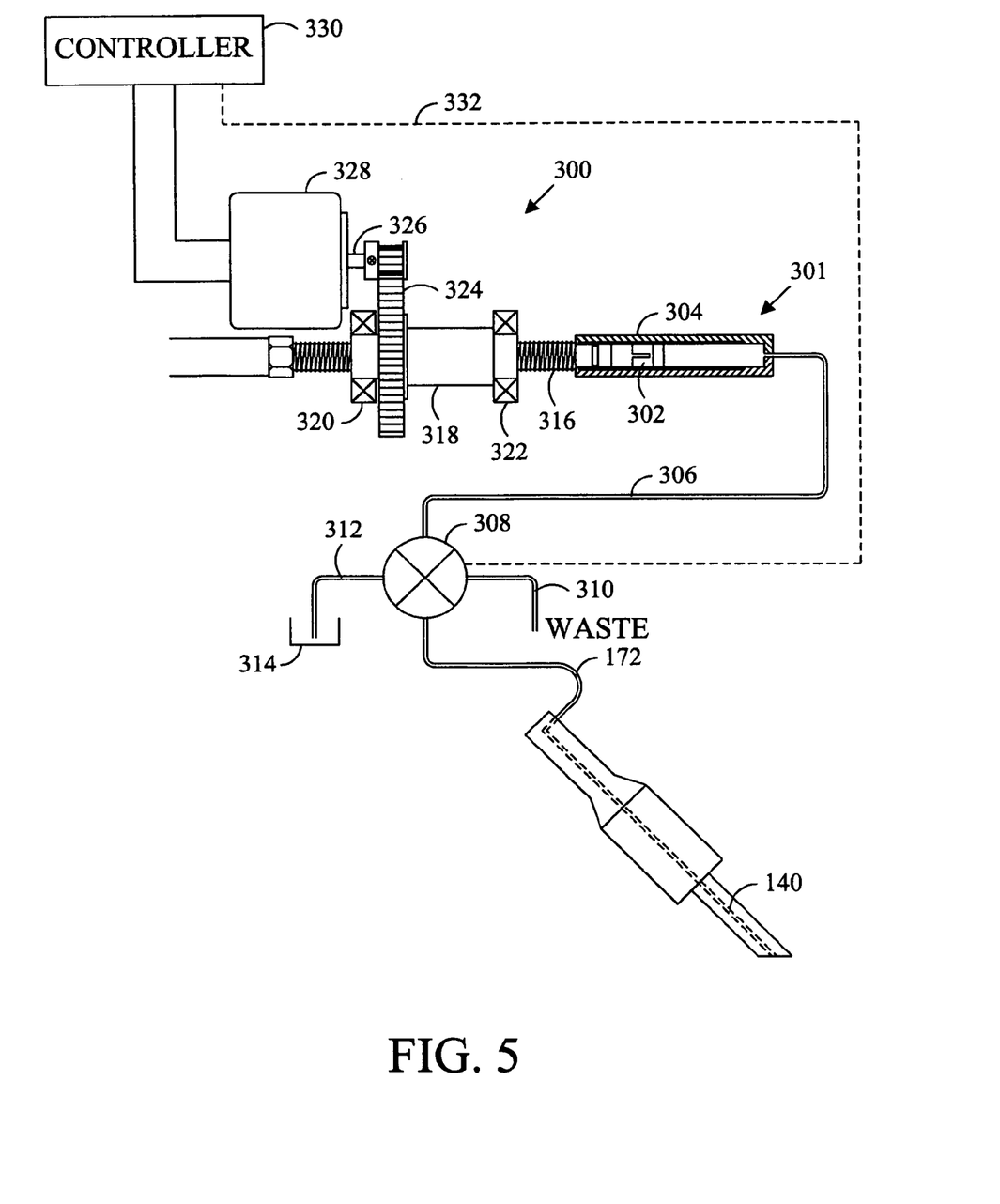
FIG. 5 is a schematic illustration of a syringe pump.

On the other hand, referring to FIG. 5, a syringe pump 300 may be used to expel fluid from the fluid delivery tube of a fluid dispensing probe. The syringe pump 300 includes a plunger 302 that is slidably sealed in a barrel 304 of a syringe 301. The barrel is connected by a conduit 306 to a valve 308 for selectively directing fluid flowing into or out of the barrel of the syringe. The valve 308 typically provides a means to selectively connect the syringe to the fluid delivery tube 306; a waste conduit 310 or conduit 312 connected a supply reservoir 314. When the reservoir 314 is selected and the plunger of the syringe is withdrawn in the barrel 304, fluid is drawn into the barrel of the syringe. When the plunger 302 is pushed into the barrel 304, fluid in the syringe is ejected to either the conduit 172 connected to the fluid delivery tube 140 or the waste conduit 310 as determined by the position of the valve 308.

Translation of a lead screw 316 connected to the plunger 302 displaces the plunger in the barrel of the syringe. Exterior threads on the lead screw 316 engage mating internal threads of a nut 318 that is rotatable in bearings 320, 322 but restrained against translation. A cogged belt 324 provides a driving connection between the rotatable shaft 326 of a motor 328 and the nut 318. Speed reduction and torque amplification can be provided by selecting the sizes of the respective pulleys on the motor shaft and the nut. Rotation of the motor shaft 326 rotates the nut 318 causing the lead screw 316 to translate along its longitudinal axis to displace the plunger of the syringe. It is desirable that the lead screw be rotatable in small increments so that the volume of the fluid ejected from the syringe can be closely controlled. Preferably the motor 328 is a stepper motor capable of stepping in increments of 10,000 or more steps per revolution under the control of a data processing device or other electronic controller 330. Feedback 332 of the valve's position is provided to the controller to ensure that the motor rotation corresponds to the selected position of the valve.

A piezoelectric device for ejecting drops of liquid from a conduit is disclosed by Arndt, U.S. Pat. No. 3,832,579, which is incorporated herein by reference. Referring to FIG. 4, a fluid to be transferred to the sample inlet well 40 of a microfluidic device 32 is stored in a reservoir 206 and path for fluid communication is provide from the reservoir to an outlet end portion 210 of the fluid delivery tube 202. The fluid delivery tube 202 comprises a material, such as glass, having a smooth interior surface and a relatively stiff wall. The fluid delivery tube comprises a first portion having a substantially uniform cross-section and a second nozzle portion 212 where the cross-section is gradually reduced to form an outlet orifice portion adjacent to the outlet end 210 of the tube. A tubular piezoelectric transducer 214 surrounds a portion of the constant cross-section portion of the fluid delivery tube 202 and is typically secured to the fluid delivery tube by epoxy cement 216. The transducer 214 includes a tubular transducer element 218 comprising a radially polarized piezoelectric material such as lead zirconate-lead titanate, and electrodes 220, 222 on the cylindrical surfaces the tubular transducer.

When ejection of an droplet is desired, a voltage pulse having a polarity to cause contraction of the transducer 214 is applied to the terminals 220, 222. The transducer contracts in response to the voltage pulse causing a decrease in the internal volume of the fluid delivery tube. This momentarily compresses a portion of the fluid in the tube and causes pressure waves to travel toward the outlet and toward the inlet of the tube. The portion of the fluid delivery tube 202 surrounded by the transducer 214 may be regarded as an acoustic transmission line. As a result of the relatively stiff walls and the uniform interior cross-section, the pressure waves are conducted without reflection in this portion of the tube. The pressure wave traveling in the direction of the outlet 210 causes ejection of a drop of fluid from the outlet.

The inlet end of the fluid delivery tube 202 is inserted into the inner diameter of an elastic tube portion 224 of the fluid supply conduit leading from the reservoir. The elastic tube portion comprises an elastic material, such as polyvinyl chloride. The nominal internal diameter of the elastic tube portion 224 of the supply conduit is less than the internal diameter in the constant cross-section portion of the fluid delivery tube 202, but the elastic tube expands to receive the fluid delivery tube. The acoustic impedance looking toward the reservoir from the inlet to the fluid delivery tube is substantially the same as the impedance in the fluid delivery tube so the pressure wave traveling toward the inlet of the fluid delivery tube is substantially unaffected by its entry into the elastic portion 224 of the conduit. However, as the pressure wave travels further into the elastic portion 224 of the conduit the diameter of the conduit gradually reduces and wave energy is absorbed by the elastic deformation of the wall of the elastic portion of the conduit. When the attenuated pressure wave reaches the reservoir 206 or a plenum 226, it encounters an impedance difference and is reflected back toward the inlet of the fluid delivery tube. However, the reflected wave is further attenuated as it travels through the elastic portion of the conduit so that it produces little or no effect on the fluid at the outlet of the fluid delivery tube.

Figure 6:
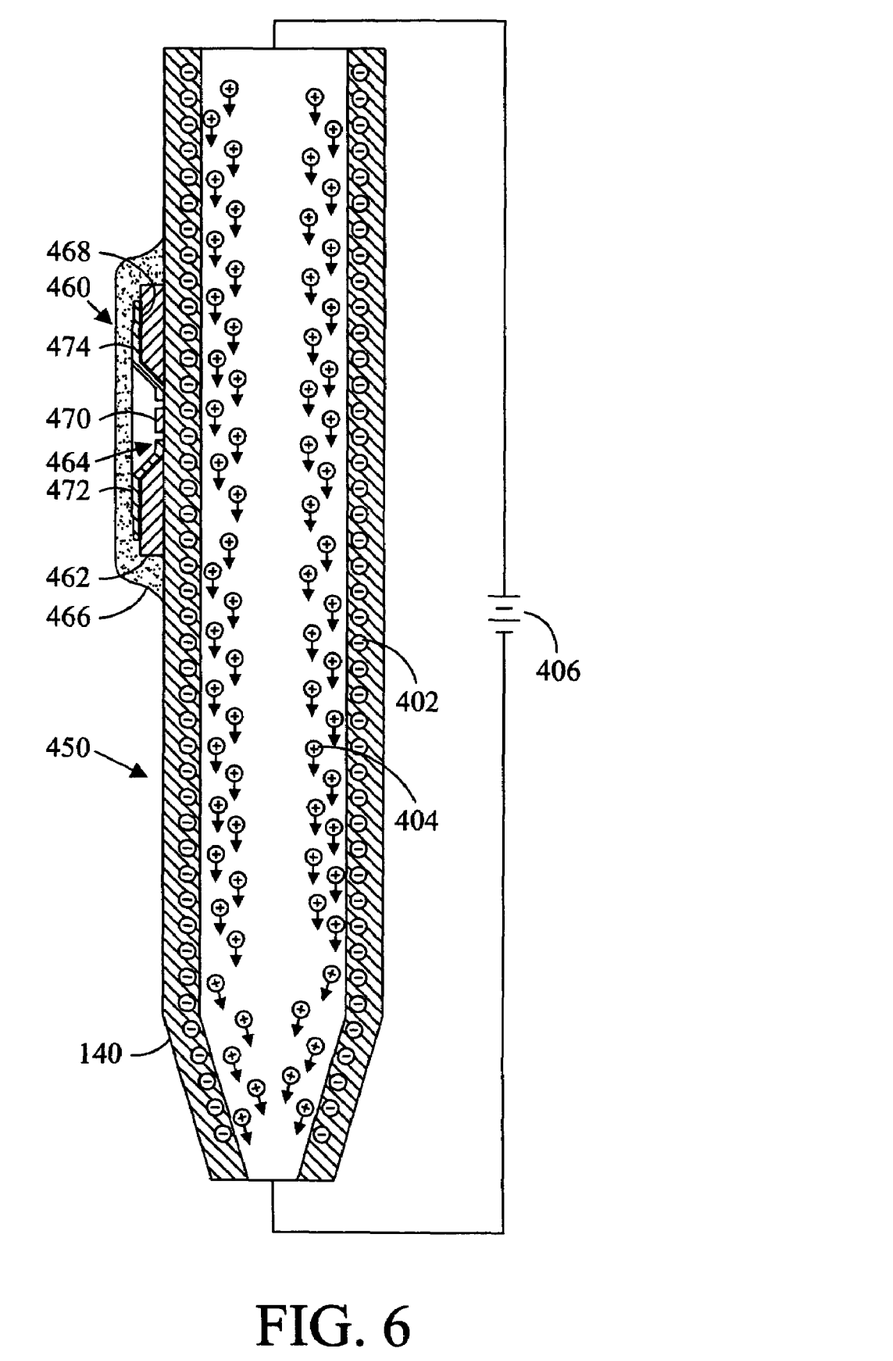
FIG. 6 is a schematic illustration of an electroosmotic pump and flow sensor.

Referring to FIG. 6, an electroosmotic pump 450 may also be used to expel fluid from the fluid delivery tube 140 to the sample inlet well 40 of a microfluidic device 32. Fluid in a capillary can be induced to flow by applying an external electric field along the length of the capillary as a result of an electrokinetic effect known as electroosmosis. Most surfaces possess a negative charge 402 as a result of ionization of the surface or absorption of ions by the surface. If the walls of the capillary fluid delivery tube 140 are negatively charged, a layer of cations 404 builds up near the wall surface to maintain the charge balance. This produces a double layer of ions near the surface and an electrical potential difference known as the zeta potential. When a voltage 406 is applied along the length of the capillary, the cations are attracted to the cathode of the voltage source. As the cations move toward cathode, they pull the bulk fluid in the capillary along with them. Increasing the voltage applied to the capillary increases the flow rate in a capillary fluid delivery tube.

To inject a sample into the sample inlet well 40 of a microfluidic device, the operator of the fluid dispensing station positions the fluid delivery tube 140 coaxial with the sample inlet well and actuates the fluid driving mechanism to eject the sample from the end of the fluid delivery tube. The end of the fluid delivery tube is moved into position by movement of the chuck, the stage and the probe positioning controls of the probe holder 116. However, the operator must commonly observe the relative positions of the end of the fluid delivery tube 140 and the sample inlet well 40 through a microscopic that is positioned above the surface of the microfluidic device. To improve visibility to the end of the fluid delivery tube, the present inventors concluded that the fluid delivery tube 140 should be arranged at an angle acute to the surface of the chuck 12 and, therefore, the microfluidic device 32.

Figure 7:
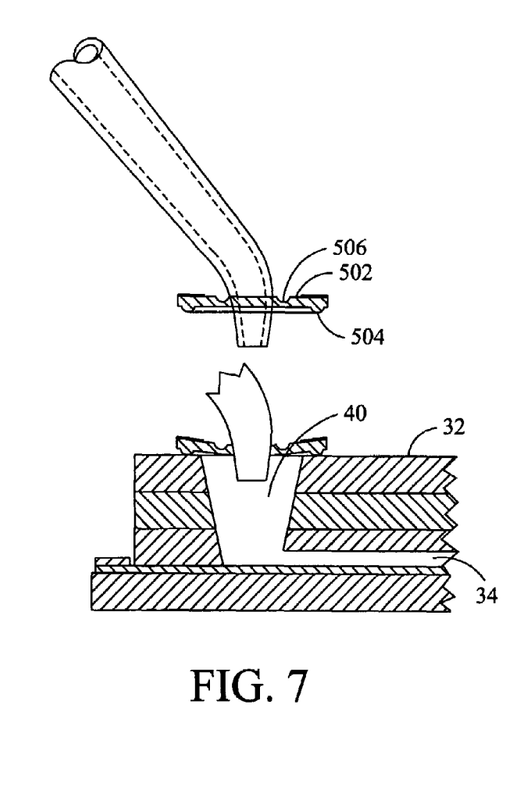
FIG. 7 is a partial section of a fluid delivery tube and seal.
Figure 8:
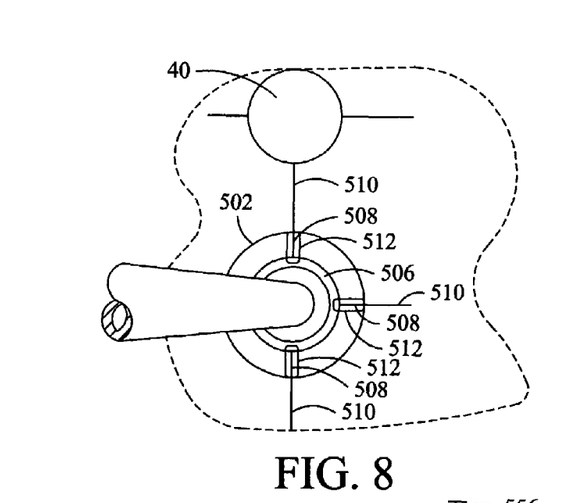
FIG. 8 is a top view of the fluid delivery tube and seal of FIG. 7.
Figure 9:
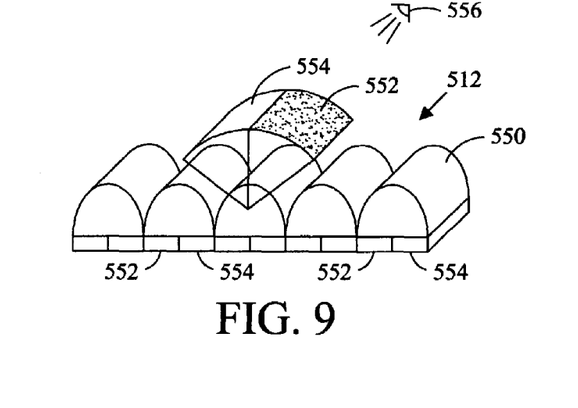
FIG. 9 is a schematic illustration of a lenticular reflector.

However, as the end of fluid delivery tube 140 and the sample inlet well 40 approach co-location, the delivery tube increasingly interferes with the operator's view of the sample inlet well. The inventors concluded that an alignment aid would improve the utility of fluid dispensing system by assisting the operator in aligning the fluid delivery tube and the sample inlet well of the microfluidic device. In addition, it is commonly desirable to seal the sample inlet well to prevent spillage when the sample is introduced and to permit pressurizing of the sample inlet well to induce the sample to flow into the microfluidic channel 34. Referring to FIGS. 7, 8 and 9, a fluid delivery tube 500 comprises a sample well seal 502 that interfaces with the surface of the microfluidic device 32 to seal the sample inlet well. The sample well seal 502 comprises a transparent, substantially annular disk of an elastic material. The lower side of the disk includes an annular seal ring 504 that protrudes from the surface of the disk to engage the surface of the microfluidic structure 30 and seal the sample inlet well 40. Enlarging the disk would permit a plurality of sample inlet wells to be sealed simultaneously. The upper surface of the disk includes an annular relief 506 that forms a hinge about which the outer portion of the disk can bend upward when the seal ring contacts the surface of the microfluidic device 32. The upper surface of the disk includes fluid delivery tube alignment marks 508 that correspond to marks 510 on the surface of the microfluidic device. Registration of the marks on the fluid delivery tube and on the microfluidic device facilitates alignment of the fluid delivery tube and the sample well.

The upper surface of the disk includes a plurality of lenticular reflectors 512. Referring to FIG. 9, the lenticular reflectors comprise a transparent sheet having a plurality of lenticules 550, linear lenses, on one side. The lenticule is shaped so that reflected light is refracted at a specific angle and magnified. Alternating strips 552, 554 of each of a plurality of images are printed on the reverse side of the sheet. The strips are aligned with the lenticules so that all of the strips of a particular image are refracted to the same point.

When the sample well seal 502 contacts the surface of the microfluidic device, the hinged portion of the seal rotates, shifting the focus point of the lenticules relative to the operator's eye 556 and shifting the image viewed by the operator from the first image to the second image. For example if the images are blocks of different colors that are printed as strips of different colors 552, 554 on the reverse side of the sheet, the color of the reflector will change to indicate to the operator that the seal is in contact with the microfluidic device.

Figure 10:
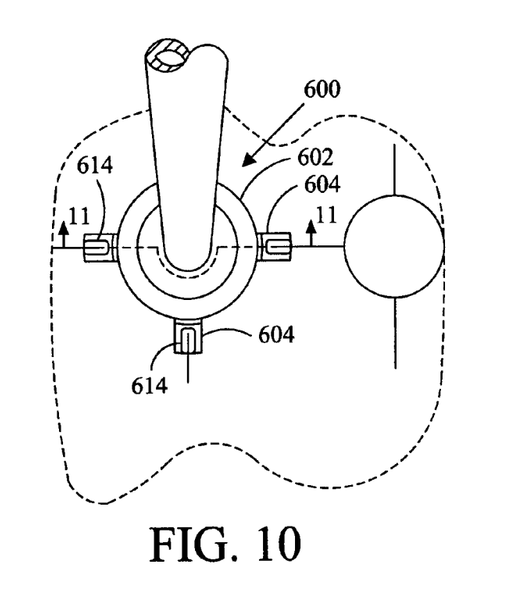
FIG. 10 is a top view of a fluid delivery tube and a second embodiment of tube end seal.
Figure 11:
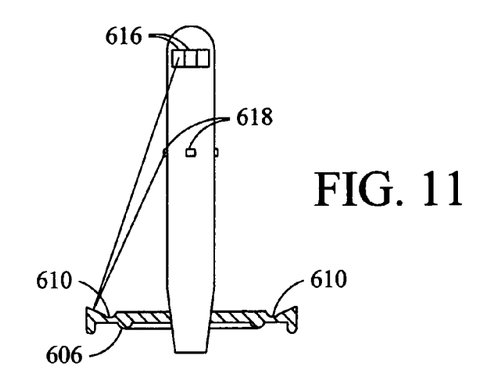
FIG. 11 is a partial elevation view of the fluid delivery tube of FIG. 10 and a seal contact detection system.
Figure 12:
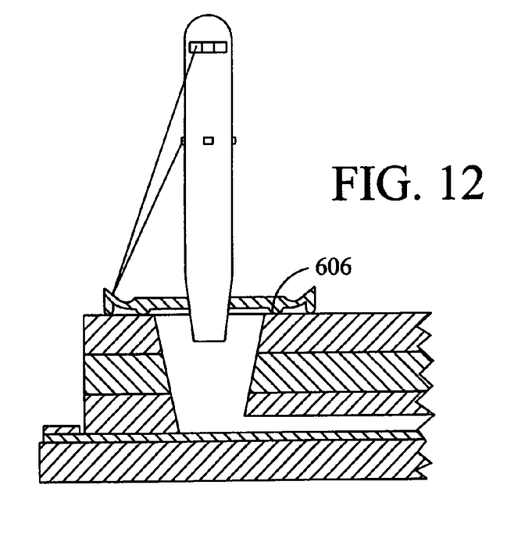
FIG. 12 is a partial section view of the fluid delivery tube and the seal contact detection system of FIG. 11.

Referring to FIGS. 10, 11 and 12, another embodiment of the fluid delivery tube seal 600 comprises a transparent, elastic disk 602 having a plurality of projecting tabs 604. An elastically deformable, circular ridge 604 projecting from the bottom surface of the disk 606 provides a compliant sample inlet well seal. The projecting tabs 604 are connected to the disk 602 by hinges 610 comprising a reduction in the cross-section of the tab. A contact point 612 projects from the bottom surface of the tab 604. The contact point 612 projects further from the plane of the lower surface of the disk than the circular seal ring 604 so that when the fluid delivery tube seal contacts the surface of the microfluidic device 32 the tabs 604 are rotated about the respective hinges. Each tab 604 also includes a reflective element 614 that will reflect light in a different direction when the seal makes contact and rotates around its hinge.

In addition, light from a source 616, for example an infrared source, is reflected to a photodetector 618 by the reflective element 614 when the tab is in the non-contact position. However, when the tab has rotated following contact with the microfluidic device 32 the reflection from the reflective element will no longer impinge on the photodetector 618. When the sample well seal 600 is properly seated on the surface of the microfluidic device 32 all of the detectors will indicate contact. However, if the seal and the surface of the microfluidic device are not co-planar, not all of the tabs will make contact at the same time. An indication that some but not all of the tabs are in contact with the microfluidic device will alert the operator to adjust the plane of the probe to achieve proper contact and sealing of the sample inlet well.

Referring again to FIG. 4, the exemplary probe 200 includes another sample well seal 230 between the end of the probe and the surface of the microfluidic device 32. The seal 230 comprises a hollow, elastic annulus including a plurality of apertures 232 connecting the interior chamber of the annulus to the surface of the seal that will contact the surface of the microfluidic device 30. Air pressure is communicated to the inner chamber of the seal through a conduit 234. Increasing air pressure in the conduit is indicative of the seal's contact with the surface of the microfluidic device and blockage of the apertures leading to the inner chamber. On the other hand, connecting a source of vacuum to the hollow interior of the seal will cause air to flow into the seal until the apertures are blocked by the surface of the microfluidic device. The change in air pressure in the conduit can be used to activate a device indicating contact by the seal. Moreover, introducing vacuum to the interior of the seal will cause the seal to adhere to the surface of the microfluidic device and promote sealing even without the application of force with the probe.

The exemplary probe 200 also comprises plenum 226 in the fluid communication path leading from the reservoir to the fluid delivery tube 202. Gas entrained in a liquid sample introduced to a microfluidic device is problematic because of the small size of the fluid passages in the device. A bubble in the sample can easily prevent the sample from flowing from the sample well into the microfluidic channel. To reduce entrained gas in a liquid sample, the sample stream is passed through a plenum that includes an electrode 228 to which a voltage is applied. Entrained gas is separated from the liquid by the electric field in the electrode and recombined by a catalyst such as palladium. To increase the surface area of the electrode 228 and enhance the separation of the gas and liquid, the electrode comprises a plurality of loops or a flat or coiled plate. An ultrasonic transducer 236 in the plenum or vibration of the electrode reduces the surface tension and prevents bubbles of gas from collecting on the electrode. The liberated gas escapes from the plenum 226 through a vent 238 that includes gas filter comprising a gas permeable but liquid impermeable membrane 240. An optical; sonic, including sonic "Q"; conductive or dielectric bubble detector 242 may be incorporated in the plenum 226 or the fluid delivery tube to monitor to the effectiveness of entrained gas separation.

In addition, the fluid delivery probe may include a flow measurement sensor. Referring to FIG. 6, a solid state flow sensor 460 of the type disclosed in U.S. Pat. No. 6,813,944 is attached to the fluid delivery tube 450. The flow sensor 460 comprises a substrate 462, retained on the exterior of the fluid delivery tube by an adhesive 466, and including a central opening 464 that is etched from the substrate and covered with a thin dielectric membrane 468. A heat source 470, typically a resistor integral with the substrate, and a pair of heat sensors 472, 474, for example thermopile sensors, are constructed in the central opening of the substrate. A controller operates the heat source which generates a heat distribution in the wall of the fluid delivery tube. Due to the flow of fluid in the fluid delivery tube, the temperature difference between the sensors of the thermopiles becomes asymmetric and a measure of the velocity of the fluid flowing in the tube.

Figure 13:
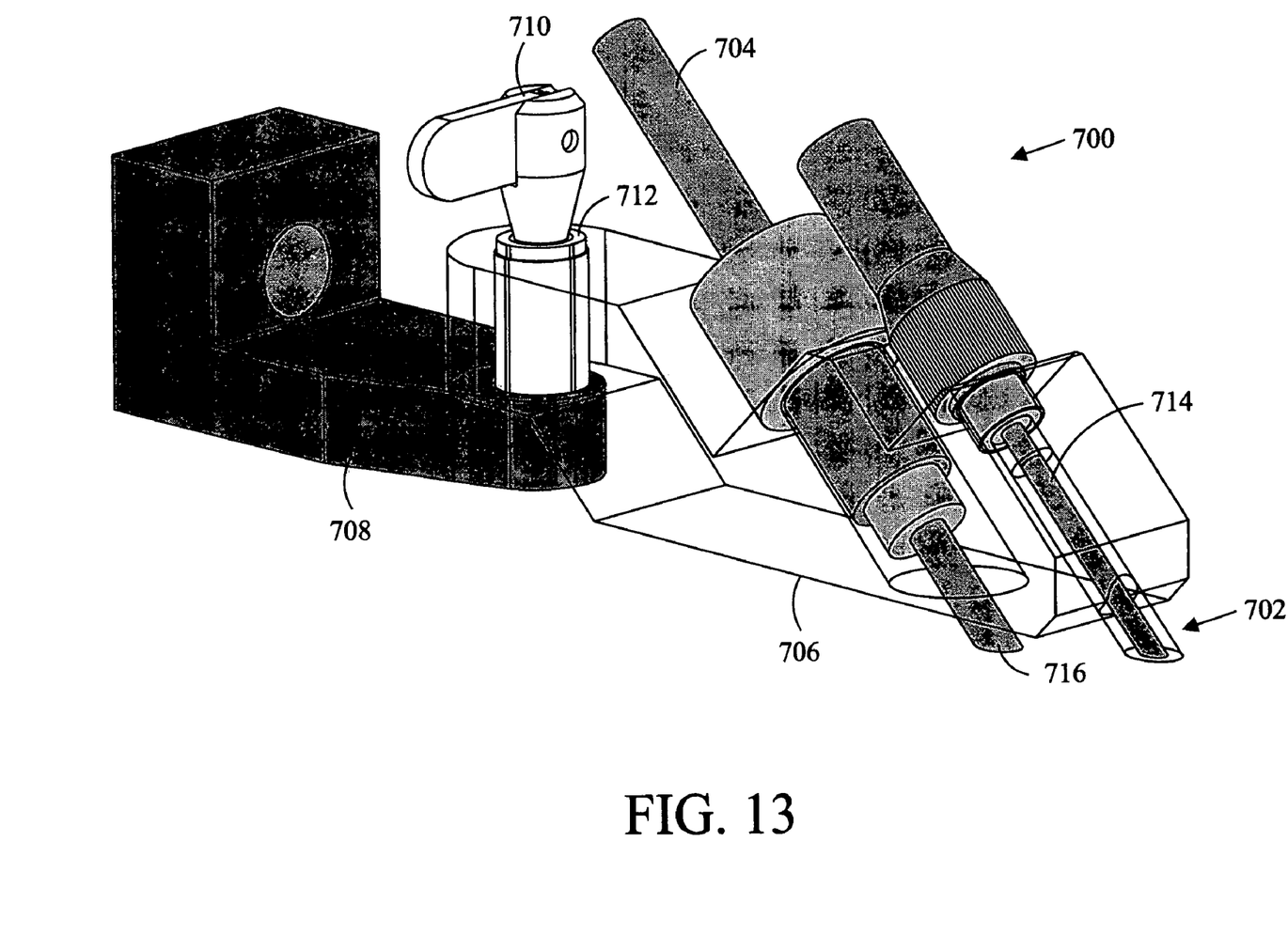
FIG. 13 is a prospective view of a combined fluid dispensing and electrical transmission probe assembly.

Referring to FIG. 13, an additional embodiment of a fluid delivery probe assembly 700 comprises a fluid delivery probe 702 and an electrical probe 704 retained in a probe fixture 706. The probe fixture 706 is attachable to the arm 708 of a probe holder by pivotal interconnection comprising a wedge bolt 710 in threaded engagement with the arm 708 of the probe holder and an expandable sleeve 712. When tightened, a tapered portion of the wedge bolt expands the sleeve 712 in an aperture in the probe fixture 706 to secure the probe to the probe holder. The fluid delivery probe 702 includes a fluid delivery tube 714 arranged at an angle to the vertical to enable better viewing of the end of the fluid delivery tube. The electrical probe 704 enables fitting electrodes 716 having one or more tips arranged to conduct electricity to and from electrical probing point(s) 60 on a microfluidic device. On the other hand, the electrical probe may be fitted with an electrode 716 that can be connected to a higher voltage source to facilitate reactions, such as, electrolysis or electrophoresis, when the end of the electrode is inserted into fluid in a fluid well of a microfluidic device.

The fluid dispensing apparatus and system facilitates dispensing small volume, fluid samples to microfluidic devices, electrically initiating reactions in microfluidic devices and monitoring the reactions within the device.

The detailed description, above, sets forth numerous specific details to provide a thorough understanding of the present invention. However, those skilled in the art will appreciate that the present invention may be practiced without these specific details. In other instances, well known methods, procedures, components, and circuitry have not been described in detail to avoid obscuring the present invention.

All the references cited herein are incorporated by reference.

The terms and expressions that have been employed in the foregoing specification are used as terms of description and not of limitation, and there is no intention, in the use of such terms and expressions, of excluding equivalents of the features shown and described or portions thereof, it being recognized that the scope of the invention is defined and limited only by the claims that follow.

The invention claimed is:

1. An apparatus for delivering a fluid to a portion of a microfluidic device defining a fluid well, said apparatus comprising:
   (a) a chuck for restraining said microfluidic device;
   (b) a probe holder comprising a fluid delivery tube support moveable relative to said chuck;
   (c) a fluid delivery tube secured to said fluid delivery tube support and having an end portion movable relative to and co-locatable with said fluid well;
   (d) a reservoir for fluid to be delivered to said fluid well, said reservoir connected for fluid flow to said fluid delivery tube;
   (e) an optical device having an optical path arranged to enable viewing of a portion of said microfluidic device proximate said fluid well when said end portion of said fluid delivery tube is co-located with said fluid well to facilitate visual observation of said end portion of said fluid delivery tube during movement relative to said fluid well;
   (f) an electrode arranged to contact a fluid in said fluid delivery tube, energizing said electrode causing liberation of a gas entrained in said fluid; and
   (g) a vent in a wall of said fluid delivery tube to enable said liberated gas to escape from said fluid delivery tube while retaining a liquid portion of said fluid in said fluid delivery tube.

2. An apparatus for delivering a fluid to a portion of a microfluidic device defining a fluid well, said apparatus comprising:
   (a) a base;
   (b) a reservoir for a quantity of fluid to be delivered to said fluid well;
   (c) a fluid transfer device having an inlet connected to said fluid reservoir and an outlet;
   (d) a fluid delivery tube having a first end in fluid communication with said outlet of said fluid transfer device and a second end arranged to be co-locatable with said portion of said microfluidic device comprising said fluid well;
   (e) a fluid delivery tube support to secure said fluid delivery tube to said base; and
   (f) a chuck secured to said base and including a restraint for said microfluidic device, at least one of said chuck and said fluid delivery tube support movable relative to said base to position said second end of said fluid delivery tube for co-location with said fluid well;
   (g) an optical device securable relative to said base having an optical path arranged to enable viewing of a portion of said microfluidic device proximate said fluid well when said end portion of said fluid delivery tube is co-located with said fluid well to facilitate visual observation of said end portion of said fluid delivery tube during movement relative to said fluid well;
   (h) an electrode arranged to contact a fluid in said fluid delivery tube, energizing said electrode causing liberation of a gas entrained in said fluid; and
   (i) a vent enabling said liberated gas to exit said fluid delivery tube while retaining a liquid portion of said fluid in said fluid delivery tube.

* * * * *